(12) United States Patent
Burke et al.

(10) Patent No.: US 8,122,778 B2
(45) Date of Patent: Feb. 28, 2012

(54) PROBE ASSEMBLY

(75) Inventors: David J. Burke, Brick, NJ (US); T. Paul Smith, Oakhurst, NJ (US); Robert T. MacRae, Freehold, NJ (US)

(73) Assignee: Perma Pure LLC, Toms River, NJ (US)

( * ) Notice: Subject to any disclaimer, the term of this patent is extended or adjusted under 35 U.S.C. 154(b) by 797 days.

(21) Appl. No.: 12/167,794

(22) Filed: Jul. 3, 2008

(65) Prior Publication Data

US 2010/0000340 A1 Jan. 7, 2010

(51) Int. Cl.
*G01N 1/00* (2006.01)
(52) U.S. Cl. ................................................. 73/863.85
(58) Field of Classification Search .................. None
See application file for complete search history.

(56) References Cited

U.S. PATENT DOCUMENTS

| | | | | |
|---|---|---|---|---|
| 5,423,228 A | * | 6/1995 | Budd et al. | 73/863.21 |
| 5,507,192 A | * | 4/1996 | Beaudin | 73/863.33 |
| 5,777,241 A | * | 7/1998 | Evenson | 73/863.11 |
| 7,368,289 B2 | | 5/2008 | Baldwin et al. | |
| 2008/0131324 A1 | | 6/2008 | Baldwin et al. | |
| 2008/0168752 A1 | | 7/2008 | Smith et al. | |
| 2008/0282764 A1 | * | 11/2008 | Holt et al. | 73/1.03 |
| 2009/0084199 A1 | * | 4/2009 | Wright et al. | 73/863.82 |

\* cited by examiner

*Primary Examiner* — Robert R Raevis
(74) *Attorney, Agent, or Firm* — Dinsmore & Shohl LLP

(57) ABSTRACT

In accordance with one embodiment of the present invention, a probe assembly comprising a flange assembly, a probe platform, a platform extension, an extension enclosure, and a fluid coupling assembly is provided. The fluid coupling assembly comprises a removable portion and a retained portion. An engaging interface of the retained portion cooperates with an engaging interface of the removable portion such that, with engagement of the removable and retained portions, respective fluid passages of the removable and retained portions form one or more integrated fluid channels configured to permit passage of fluid through the fluid coupling assembly. The probe assembly is configured such that the probe platform, the platform extension, and the removable portion of the fluid coupling assembly are interconnected and are configured to be withdrawn simultaneously from the probe assembly independent of the retained portion of the fluid coupling assembly.

19 Claims, 4 Drawing Sheets

US 8,122,778 B2

PROBE ASSEMBLY

BRIEF SUMMARY

The present invention relates generally to probe assemblies and, more particularly, to probe assemblies that are configured to be mounted to an exhaust stack such that an analytical probe can be projected into a flow of particulate-containing gas passing through the exhaust stack. The probe assembly may be configured such that a series of interconnected components may be simultaneously withdrawn from the probe assembly independent of other components of the probe assembly.

In accordance with one embodiment of the present invention, the probe assembly comprises a flange assembly, a probe platform, a platform extension, an extension enclosure, and a fluid coupling assembly. The flange assembly is configured to mount the probe assembly to a stack fixture assembly of an exhaust stack, while the extension enclosure is configured to extend into a flow of particulate-containing gas passing through the exhaust stack when the probe assembly is mounted to the exhaust stack. The probe platform is configured to support an analytical probe and the platform extension at least partially supports the probe platform in the vicinity of a distal end of the extension enclosure. The fluid coupling assembly, meanwhile, comprises a removable portion and a retained portion. The removable portion of the fluid coupling assembly comprises one or more disengageable fluid passages extending from an engaging interface of the removable portion to an input/output interface of the removable portion, while the retained portion of the fluid coupling assembly comprises one or more retained fluid passages extending from an input/output interface of the retained portion to an engaging interface of the retained portion. The engaging interface of the retained portion cooperates with the engaging interface of the removable portion such that, with engagement of the removable and retained portions of the fluid coupling assembly, the respective fluid passages of the removable and retained portions of the fluid coupling assembly form one or more integrated fluid channels configured to permit passage of fluid through the fluid coupling assembly. The probe platform, the platform extension, and the removable portion of the fluid coupling assembly are interconnected and are configured to be withdrawn simultaneously from the probe assembly independent of the retained portion of the fluid coupling assembly.

In accordance with another embodiment of the present invention, a probe assembly further comprises a handle and a coupling bracket. The coupling bracket is configured to couple the handle to the removable portion of the fluid coupling assembly and to couple the removable portion of the fluid coupling assembly to the platform extension. As such, the probe platform, the platform extension, the removable portion of the fluid coupling assembly, the coupling bracket, and the handle are interconnected and are configured to be withdrawn simultaneously from the probe assembly independent of the retained portion of the fluid coupling assembly. The handle is positioned for gripping to assist with the simultaneous withdrawal of the interconnected probe platform, platform extension, removable portion of the fluid coupling assembly, handle, and coupling bracket from the probe assembly.

BRIEF DESCRIPTION OF THE SEVERAL VIEWS OF THE DRAWINGS

The following detailed description of specific embodiments of the present invention can be best understood when read in conjunction with the following drawings, where like structure is indicated with like reference numerals and in which.

Figure 1:
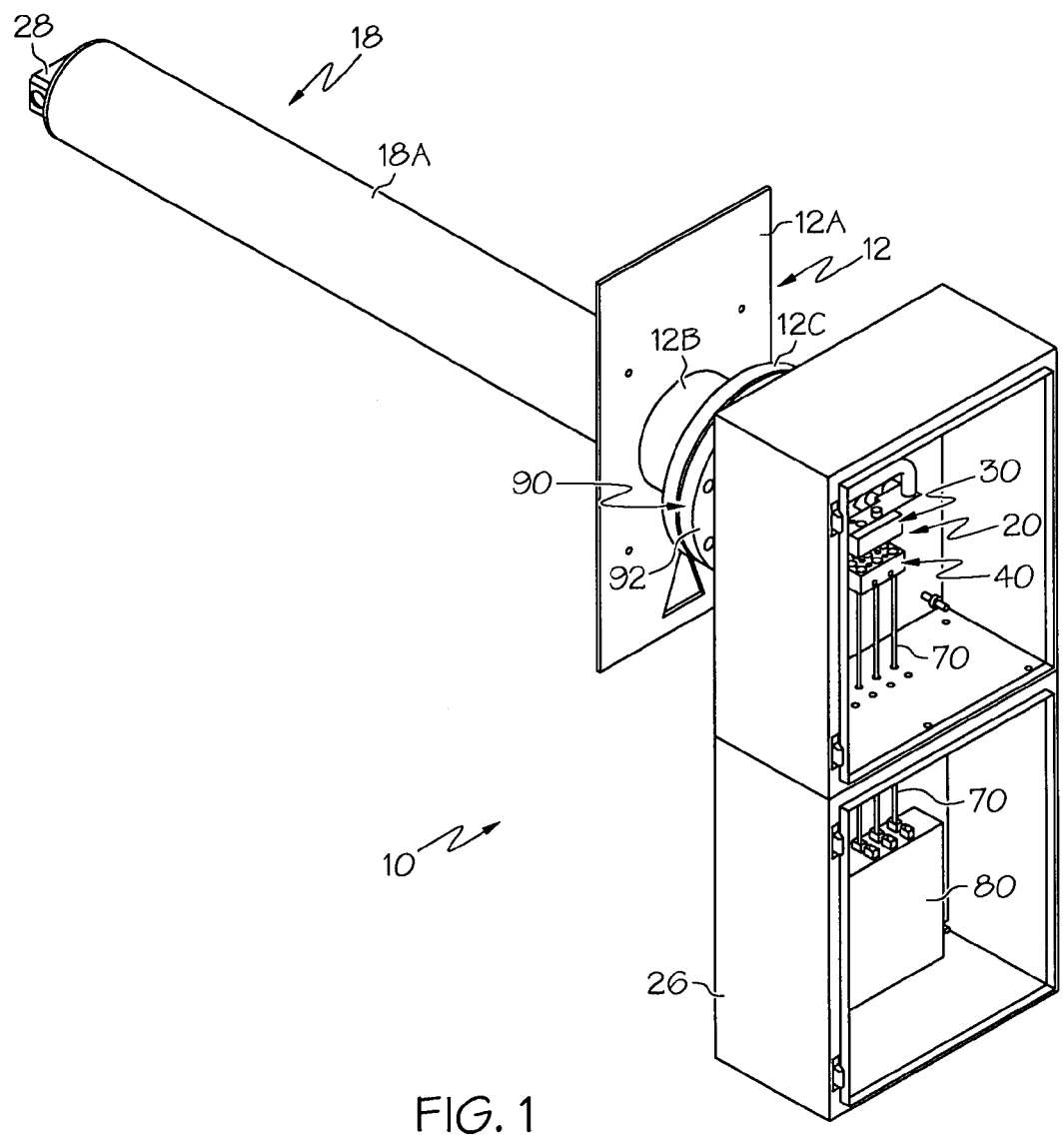
FIG. 1 is an illustration of a probe assembly according to one embodiment of the present invention.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION

Referring initially to FIG. 1, a probe assembly 10 may be used to assist in gas and/or particle analysis of a particulate-containing gas flow passing through an exhaust stack. This probe assembly 10 generally comprises a flange assembly 90, a probe platform 14, a platform extension 16, an extension enclosure 18, and a fluid coupling assembly 20. The probe assembly 10 may also comprise a handle 22, a coupling bracket 24, and a control box 26. The probe assembly 10 is configured such that the probe platform 14, and any analytical probe supported thereon, the platform extension 16, and a removable portion 30 of the fluid coupling assembly 20 are interconnected and are configured to be withdrawn simultaneously from the probe assembly 10 independent of a retained portion 40 of the fluid coupling assembly 20.

The flange assembly 90 generally is configured to mount the probe assembly 10 to a stack fixture assembly 12 of an exhaust stack. The stack fixture assembly 12 is mounted about an opening in a wall of an exhaust stack. The stack fixture 12, shown in FIG. 1, generally comprises a stack fixture plate 12A, a stack fixture pipe 12B, and a stack fixture flange 12C. The stack fixture plate 12A may be configured to secure to the wall of the exhaust stack and to seal off the opening in the wall of the exhaust stack such that substantially no gas flow passing though the exhaust stack exits the stack through this opening, other than a portion of the gas sampled and/or analyzed by an analytical probe 28 supported by the probe assembly 10. The stack fixture pipe 12B couples the stack fixture plate 12A and the stack fixture flange 12C, which generally is exposed along an exterior of the wall of the exhaust stack.

Figure 3:
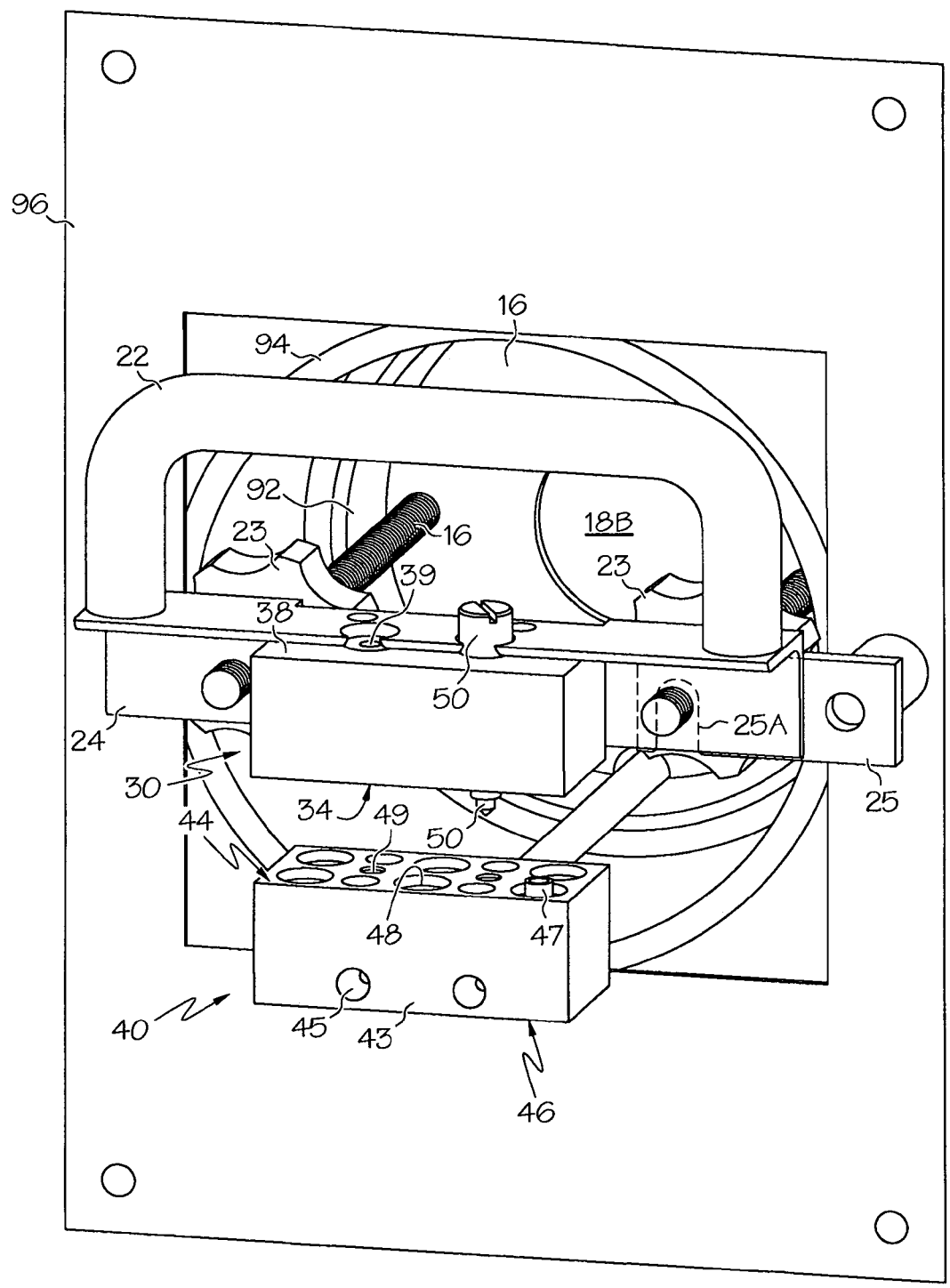
FIG. 3 is an illustration of a fluid coupling assembly, a handle, a coupling bracket, and a platform extension of a probe assembly according to one embodiment of the present invention.

The flange assembly 90, shown in FIGS. 1 and 3, generally comprises a flange 92, a pipe 94, and a plate 96. The flange 92 of the flange assembly 90 may be configured to secure the probe assembly 10 to the stack fixture flange 12C so as to mount the probe assembly 10 to the exhaust stack. The plate 96 may be configured to secure to the control box 26 of the probe assembly 10, while the pipe 94 may be configured to couple the flange 92 and the plate 96 and to permit passage therethrough of the extension enclosure 18 of the probe assembly 10. Thereby, various components, such as the probe platform 14, at least a portion of the platform extension 16, and at least a portion of the extension enclosure 18, may be positioned in an interior of the exhaust stack, while various other components, such as the fluid coupling assembly 20, the handle 22, the coupling bracket 24, and the control box 26, may be positioned along an exterior of the exhaust stack.

The extension enclosure 18 generally traverses through the pipes 94, 12B of the flange assembly 90 and the stack fixture assembly 12, respectively. As such, the extension enclosure 18 may be configured to extend into a flow of particulate-containing gas passing through the exhaust stack when the probe assembly 10 is mounted to the exhaust stack. The extension enclosure 18 generally is configured as having an outer shell 18A that encloses a channel 18B extending along a longitudinal axis of the extension enclosure 18. As such, the extension enclosure 18 may be configured to support and substantially enclose the platform extension 16. Further, while the extension enclosure 18 is illustrated in FIGS. 1 and 2 as having a circular, or substantially circular, cross-section, it is contemplated that the extension enclosure 18 may have any cross-sectional shape configured to support and substantially enclose the platform extension 16 and to extend into a flow of particulate-containing gas passing through the exhaust stack.

Figure 2:
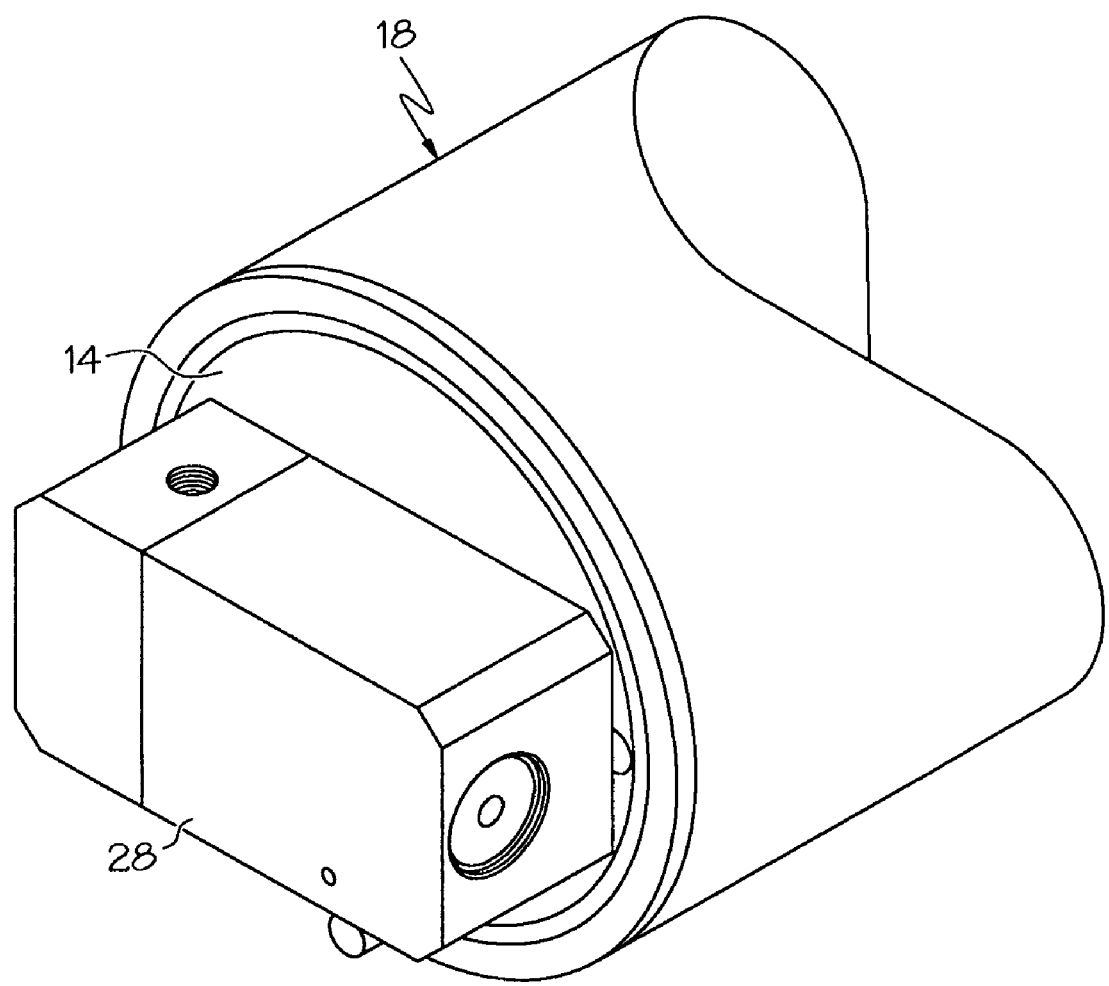
FIG. 2 is an illustration of a magnified view of an analytical probe and a probe platform of a probe assembly according to one embodiment of the present invention.

As shown in FIGS. 1 and 2, the probe platform 14 generally is configured to support the analytical probe 28. Generally, both the probe platform 14 and the analytical probe 28 are sized to pass through the channel of the extension enclosure 18. The analytical probe 28 may be a gas-separating apparatus configured to separate the particulate-containing gas flow passing through the exhaust stack into a particulate-containing gas flow portion and a substantially particulate-free gas flow portion. It is contemplated, however, that the probe platform 14 and probe assembly 10 may support any analytical probe configured to sample and/or analyze gas and/or particulate matter derived from a particulate-containing gas flow.

As described above, and as illustrated in FIG. 3, the platform extension 16 generally is substantially enclosed by the extension enclosure 18. As shown in FIG. 3, the platform extension 16 generally comprises one or more rods and one or more channeled plates that extend through the channel 18B of the extension enclosure 18. More particularly, in one embodiment, the platform extension 16 substantially traverses a length of the extension enclosure 18 such that the platform extension 16 extends from the vicinity of an end of the extension enclosure 18 distal from the flange assembly 90 through an end of the extension enclosure 18 proximal to the flange assembly 90. Thereby, the platform extension 16 at least partially supports the probe platform 14 in the vicinity of the distal end of the extension enclosure 18.

Figure 4:
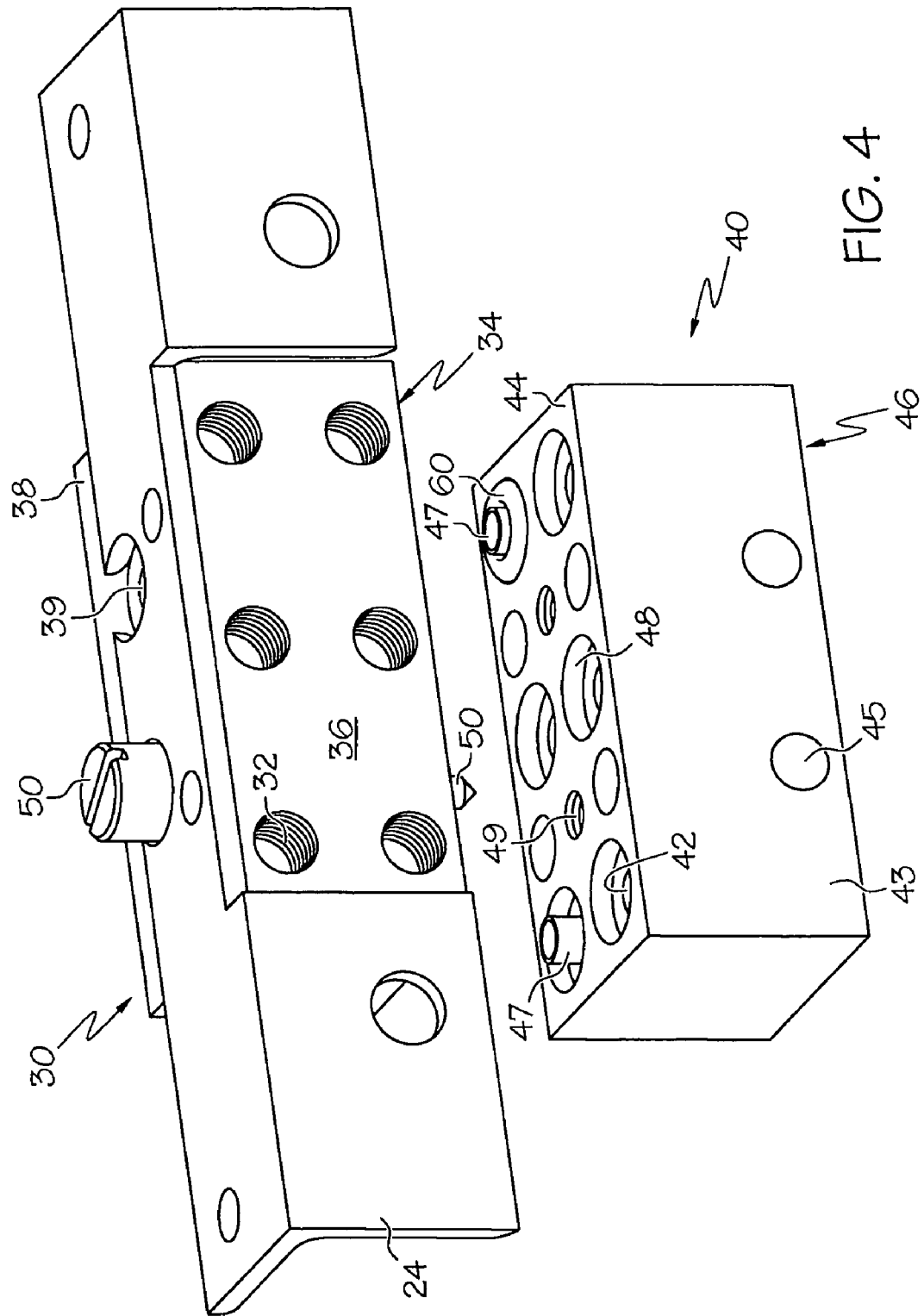
FIG. 4 is an illustration of an isolated view of a fluid coupling assembly and a coupling bracket of a probe assembly according to one embodiment of the present invention.

As shown in FIGS. 1, 3, and 4, the fluid coupling assembly 20 comprises a removable portion 30 and a retained portion 40. The removable portion 30 of the fluid coupling assembly 20 comprises one or more disengageable fluid passages 32 extending from an engaging interface 34 of the removable portion 30 to an input/output interface 36 of the removable portion 30. The removable portion 30 of the fluid coupling assembly 20 generally is configured such that the engaging interface 34 of the removable portion 30 and the input/output interface 36 of the removable portion 30 are oriented in non-parallel or substantially orthogonal planes. As such, in this embodiment, the disengageable fluid passages 32 may extend in an angulated or arced path, such as forming a 90° angle or otherwise. It is contemplated, however, that the removable portion 30 of the fluid coupling assembly 20 may be configured such that the engaging interface 34 of the removable portion 30 and the input/output interface 36 of the removable portion 30 are oriented in parallel planes. In this embodiment, the disengageable fluid passages 32 may extend in a linear path.

The retained portion 40 of the fluid coupling assembly 20 comprises one or more retained fluid passages 42 extending from an input/output interface 46 of the retained portion 40 to an engaging interface 44 of the retained portion 40. The retained portion 40 generally is configured such that the engaging interface 44 of the retained portion 40 and the input/output interface 46 of the retained portion 40 are oriented in parallel planes. As such, in this embodiment, the retained fluid passages 42 may extend in a linear path. It is contemplated, however, that the engaging interface 44 and the input/output interface 46 may be oriented in non-parallel or substantially orthogonal planes. As such, the retained fluid passages 42 may extend in an angulated or arced path, such as forming a 90° angle or otherwise.

The engaging interface 44 of the retained portion 40 of the fluid coupling assembly 20 cooperates with the engaging interface 34 of the removable portion 30 of the fluid coupling assembly 20 such that, with engagement of the removable and retained portions 30, 40, the respective fluid passages 32, 42 of the removable and retained portions 30, 40 form one or more integrated fluid channels configured to permit passage of fluid through the fluid coupling assembly 20. Further, the engaging interface 34 or 44 of one of the removable and retained portions 30, 40 of the fluid coupling assembly 20 may comprise a recess 48 and a sealing insert 47 proximal to one or more of the fluid passages 32 or 42. The sealing insert 47 may be configured to insert at least partially into the fluid passages 32 or 42 of the other of the removable and retained 30, 40 portions of the fluid coupling assembly 20 with the engagement of the removable and retained portions 30, 40. The recess 48, meanwhile, may be recessed in the engaging interface 34 or 44 and separated from the fluid passages 32 or 42 by the sealing insert 47.

For illustrative purposes, in FIGS. 1, 3, and 4, the retained portion 40 of the fluid coupling assembly 20 has been vertically offset from a position where generally it would be engaged with the removable portion 30 of the fluid coupling assembly 20. In FIGS. 1, 3, and 4, the retained portion 40 is vertically offset simply to clearly illustrate the engaging interface 44 of the retained portion 40, the sealing insert 47, and the recesses 48. Further, while FIGS. 3 and 4 illustrate an embodiment where the sealing insert 47 and the recess 48 are integrated into the engaging interface 44 of the retained portion 40 of the fluid coupling assembly 20, it is contemplated that the sealing insert 47 and the recess 48 may alternatively be integrated into the engaging interface 34 of the removable portion 30 of the fluid coupling assembly 20. In addition, while FIGS. 3 and 4 illustrate one or two sealing inserts 47, respectively, on the engaging surface 44, it is contemplated that a sealing insert 47 may be provided proximal to each retained fluid passage 42 in the retained portion 40 of the fluid coupling assembly 20.

The fluid coupling assembly 20 may further comprise a gasket 60 positionable in the recess 48 of the removable or retained portion 30, 40. Thereby, the gasket 60 may substantially prevent fluid leakage between the engaging interfaces 34, 44 of the removable and retained portions 30, 40 of the fluid coupling assembly 20 and does not interfere with fluid passage through the fluid coupling assembly 20 with engagement of the removable and retained portions 30, 40. The gasket 60 may be an o-ring or any other sealing device.

The input/output interfaces 36, 46 of the removable and retained portions 30, 40 of the fluid coupling assembly 20 are configured to connect to hoses, tubing, or other fluid conveying devices 70. The points of connection between the input/output interfaces 36, 46 and the fluid conveying devices 70 are in communication with the fluid passages 32, 42 of the removable and retained portions 30, 40. Thereby, fluid may be directed to/from the input/output interfaces 36, 46 by the fluid conveying devices 70 and may pass through the integrated fluid channels formed in the fluid coupling assembly 20 with the engagement of the removable and retained portions 30, 40. It is contemplated that the points of connection with the fluid conveying devices 70 may be simply the openings of the fluid passages 32, 42, or ports integrated therewith, in the engaging 34, 44 and input/output 36, 46 interfaces of the removable and retained portions 30, 40 of the fluid coupling assembly 20. It is further contemplated that the removable and retained portions 30, 40 may comprise any number of fluid passages 32, 42 and points of connection for connecting with fluid conveying devices 70. For example, but not by way of limitation, in one embodiment, the removable and retained portions 30, 40 each have two fluid passages 32, 42 and points of connection, while, in another embodiment, the removable and retained portions 30, 40 each have six fluid passages 32, 42 and points of connection.

The removable portion 30 of the fluid coupling assembly 20 may also comprise a securing interface 38. This securing interface 38 may comprise a plurality of disengageable apertures 39, at least one of which extends from the securing interface 38 to the engaging interface 34 of the removable portion 30. In addition, the engaging interface 44 of the retained portion 40 of the fluid coupling assembly 20 may comprise one or more retained apertures 49. The retained apertures 49 may be configured to cooperate with one or more of the plurality of disengageable apertures 39 in releasably securing the engagement of the removable and retained portions 30, 40 with securing hardware 50. Further, the retained portion 40 may comprise a securing interface 43. This securing interface 43 may be configured to permit passage of securing hardware through securing passages 45 for the mounting of the retained portion 40 to the probe assembly 10, directly to the exhaust stack, or otherwise.

As mentioned above, the probe assembly 10 may also comprise a coupling bracket 24 and a handle 22. At least one of the disengageable apertures 39 of the securing interface 38 of the removable portion 30 of the fluid coupling assembly 20 may be configured to permit the insertion of securing hardware for the mounting of the coupling bracket 24. Thus, the coupling bracket 24 may be mounted to the securing interface 38 of the removable portion 30 of the fluid coupling assembly 20.

The coupling bracket 24 is configured to secure the handle 22 to the removable portion 30 of the fluid coupling assembly 20. Further, the coupling bracket 24 is configured to secure the removable portion 30 of the fluid coupling assembly 20 to the platform extension. As such, the probe platform 14, the platform extension 16, the removable portion 30 of the fluid coupling assembly 20, the handle 22, and the coupling bracket 24 are interconnected and configured to be withdrawn simultaneously from the probe assembly 10 independent of the retained portion 40 of the fluid coupling assembly 20.

The handle 22, meanwhile, is positioned for gripping to assist with the simultaneous withdrawal of the interconnected probe platform 14, platform extension 16, removable portion 30 of the fluid coupling assembly 20, handle 22, and coupling bracket 24 of the probe assembly 10. The handle 22 is shown in FIGS. 1, 3, and 4 in a U-shaped configuration. It is contemplated, however, that the handle may be provided in any configuration that may be gripped, by tool or by hand, and may assist in the simultaneous withdrawal described above.

As also mentioned above, the probe assembly 10 may further comprise a control box 26. The control box 26 generally is configured to mount to the wall of the exhaust stack removed from the particulate-containing gas flow passing therethrough. Further, the control box 26 is configured to house the fluid coupling assembly 20 and a flow control system. The flow control system may be configured to control gas flow substantially throughout the probe assembly 10. More particularly, the flow control system may control blowing gas flow and vacuum draw flow through the fluid coupling assembly 20 to/from the analytical probe 28. As such, the flow control system comprises equipment necessary to achieve these stated purposes. For example, the flow control system may comprise a pump 80, at least one flow control valve, and a plurality of hoses or other fluid conveying devices 70. The fluid conveying devices 70 are in communication with the analytical probe 28, the fluid coupling assembly 20, and analytical equipment configured to measure a variable of the gas or particulate matter sampled/analyzed by the probe 28.

As described herein, the probe platform 14, the platform extension 16, and the removable portion 30 of the fluid coupling assembly 20 may be interconnected and withdrawn simultaneously from the probe assembly 10 independent of the retained portion 40 of the fluid coupling assembly. To simultaneously withdraw these interconnected components 14, 16, 30 of the probe assembly 10, the removable and retained portions 30, 40 can be disengaged. Generally, to achieve this disengagement, thumb screws 23 are loosened so as to relieve applied pressure between the coupling bracket 24 and one or more support brackets 25. While only one support bracket 25 is visible in FIG. 3, the probe assembly 10 generally comprises two support brackets 25 laterally disposed on opposite ends of the coupling bracket 24. The support brackets 25 generally are rotatably coupled to the control box 26 and are configured to rotate such that slot 25A is positioned at least partially about the rods of the platform extension 16 that connect the platform extension 16 to the fluid coupling assembly 20, as shown in FIG. 3. Thereby, the support brackets 25 may be positioned between the thumb screws 23 and the coupling bracket 24. The applied pressure is provided by rotating the thumb screws 23 in a tightening direction of rotation along rods of the platform extension 16 so as to compress the support brackets 25 against the coupling bracket 24. In relieving the applied pressure with the loosening of the thumb screws 23, the support brackets 25 may be rotated away from the rods of the platform extension 16 and from between coupling bracket 24 and the thumb screws 23. Thereby, the support brackets 25 are no longer providing any support to the coupling bracket 24 and will not obstruct the simultaneous withdrawal of the platform extension 16 and probe platform 14 from the channel 18B of the extension enclosure 18.

In addition, to disengage the removable and retained portions 30, 40 of the fluid coupling assembly 20, securing hardware 50 that passes through the disengageable apertures 39 of the removable portion 30 and into the retained apertures 49 of the retained portion 40 is loosened or removed such that the securing hardware 50 is no longer inserted into the retained apertures 49. Thereby, the removable portion 30, and the platform extension 16 and probe platform 14 interconnected therewith, may be lifted slightly upward, by the handle 22 or otherwise, so as to disengage the removable portion 30 and the retained portion 40 of the fluid coupling assembly 20. In practicing the present invention, it is contemplated that a variety of alternative securing hardware configurations may be employed to permit the aforementioned simultaneous withdrawal of the interconnected components 14, 16, 30 of the probe assembly 10, independent of the retained portion 40 of the fluid coupling assembly 20. For example, the retained portion 40 may be configured to be shiftable in a downward direction, allowing the user to remove the interconnected components 14, 16, 30 of the probe assembly 10 without the aforementioned upward lifting motion.

Once the removable and retained 30, 40 portions of the fluid coupling assembly 20 are disengaged, the interconnected removable portion 30, platform extension 16, and probe platform 14 may be withdrawn simultaneously from the retained portion 40 of the fluid coupling assembly 20 and the probe assembly 10 by lifting and/or pulling in a substantially laterally direction at the handle 22 or otherwise. Fluid conveying devices coupling the removable portion 30 to the analytical probe 28 may also be withdrawn simultaneously with these interconnected components 14, 16, 30 from the probe assembly 10. These interconnected components 14, 16, 30 may be withdrawn for cleaning, repair, replacement, testing, or other purposes. It is also contemplated that other components of the probe assembly 10, such as, but not limited to, the retained portion 40 of the fluid coupling assembly 20, the fluid conveying devices 70 coupled to the retained portion, and the control box 26, may be removed from the probe assembly 10 for the same or similar purposes.

It is noted that recitations herein of a component of the present invention being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is noted that terms like "generally" and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A probe assembly comprising a flange assembly, a probe platform, a platform extension, an extension enclosure, and a fluid coupling assembly, wherein:
the flange assembly is configured to mount the probe assembly to a stack fixture assembly of an exhaust stack;
the extension enclosure is configured to extend into a flow of particulate-containing gas passing through the exhaust stack when the probe assembly is mounted to the exhaust stack;
the probe platform is configured to support an analytical probe;
the platform extension at least partially supports the probe platform in the vicinity of a distal end of the extension enclosure;
the fluid coupling assembly comprises a removable portion and a retained portion;
the removable portion of the fluid coupling assembly comprises one or more disengageable fluid passages extending from an engaging interface of the removable portion to an input/output interface of the removable portion;
the removable portion of the fluid coupling assembly is configured such that the engaging interface of the removable portion and the input/output interface of the removable portion are oriented in non-parallel or substantially orthogonal planes;
the retained portion of the fluid coupling assembly comprises one or more retained fluid passages extending from an input/output interface of the retained portion to an engaging interface of the retained portion;
the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly; and
the probe platform, the platform extension, and the removable portion of the fluid coupling assembly are interconnected and are configured to be withdrawn simultaneously from the probe assembly independent of the retained portion of the fluid coupling assembly.

2. The probe assembly of claim 1, wherein the removable portion of the fluid coupling assembly is configured such that the engaging interface of the removable portion and the input/output interface of the removable portion are oriented in parallel planes.

3. The probe assembly of claim 1, wherein the retained portion of the fluid coupling assembly is configured such that the engaging interface of the retained portion and the input/output interface of the retained portion are oriented in parallel planes.

4. The probe assembly of claim 1, wherein the input/output interfaces of the removable and retained portions of the fluid coupling assembly are configured to connect to hoses, tubing, or other fluid conveying devices.

5. The probe assembly of claim 1, wherein the analytical probe is a gas-separating apparatus configured to separate the particulate-containing gas flow into a particulate-containing gas flow portion and a substantially particulate-free gas flow portion.

6. The probe assembly of claim 1, wherein the probe assembly further comprises a control box configured to house the fluid coupling assembly and a flow control system configured to control gas flow substantially throughout the probe assembly.

7. The probe assembly of claim 6, wherein the flange assembly comprises:
a flange configured to secure the probe assembly to a flange of the stack fixture assembly of the exhaust stack,
a plate configured to secure to the control box of the probe assembly, and a pipe configured to couple the flange and the plate and to permit passage therethrough of the extension enclosure of the probe assembly.

8. A probe assembly comprising a flange assembly, a probe platform, a platform extension, an extension enclosure, and a fluid coupling assembly, wherein:

the flange assembly is configured to mount the probe assembly to a stack fixture assembly of an exhaust stack;

the extension enclosure is configured to extend into a flow of particulate-containing gas passing through the exhaust stack when the probe assembly is mounted to the exhaust stack;

the probe platform is configured to support an analytical probe;

the platform extension at least partially supports the probe platform in the vicinity of a distal end of the extension enclosure;

the fluid coupling assembly comprises a removable portion and a retained portion;

the removable portion of the fluid coupling assembly comprises one or more disengageable fluid passages extending from an engaging interface of the removable portion to an input/output interface of the removable portion;

the retained portion of the fluid coupling assembly comprises one or more retained fluid passages extending from an input/output interface of the retained portion to an engaging interface of the retained portion;

the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly;

the probe platform, the platform extension, and the removable portion of the fluid coupling assembly are interconnected and are configured to be withdrawn simultaneously from the probe assembly independent of the retained portion of the fluid coupling assembly;

the engaging interface of one of the removable and retained portions of the fluid coupling assembly comprises a recess and a sealing insert proximal to one or more fluid passages;

the sealing insert is configured to insert at least partially into the fluid passage of the other of the removable and retained portions of the fluid coupling assembly with the engagement of the removable and retained portions; and the recess is recessed in the engaging interface and is separated from the fluid passages by the sealing insert.

9. The probe assembly of claim 8, wherein the fluid coupling assembly further comprises a gasket positionable in the recess such that the gasket substantially prevents fluid leakage between the engaging interfaces of the removable and retained portions of the fluid coupling assembly and does not interfere with fluid passage through the fluid coupling assembly with engagement of the removable and retained portions.

10. A probe assembly comprising a flange assembly, a probe platform, a platform extension, an extension enclosure, and a fluid coupling assembly, wherein:

the flange assembly is configured to mount the probe assembly to a stack fixture assembly of an exhaust stack;

the extension enclosure is configured to extend into a flow of particulate-containing gas passing through the exhaust stack when the probe assembly is mounted to the exhaust stack;

the probe platform is configured to support an analytical probe;

the platform extension at least partially supports the probe platform in the vicinity of a distal end of the extension enclosure;

the fluid coupling assembly comprises a removable portion and a retained portion;

the removable portion of the fluid coupling assembly comprises one or more disengageable fluid passages extending from an engaging interface of the removable portion to an input/output interface of the removable portion;

the retained portion of the fluid coupling assembly comprises one or more retained fluid passages extending from an input/output interface of the retained portion to an engaging interface of the retained portion;

the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly;

the probe platform, the platform extension, and the removable portion of the fluid coupling assembly are interconnected and are configured to be withdrawn simultaneously from the probe assembly independent of the retained portion of the fluid coupling assembly;

the removable portion of the fluid coupling assembly comprises a securing interface comprising a plurality of disengageable apertures, at least one of the plurality of disengageable apertures extending from the securing interface to the engaging interface of the removable portion; and the engaging interface of the retained portion of the fluid coupling assembly comprises one or more retained apertures configured to cooperate with one or more of the plurality of disengageable apertures in releasably securing the engagement of the removable and retained portions with securing hardware.

11. The probe assembly of claim 10, wherein at least one of the disengageable apertures of the securing interface of the removable portion is configured to permit the insertion of securing hardware for mounting a coupling bracket to the securing interface of the removable portion of the fluid coupling assembly.

12. The probe assembly of claim 11, wherein the coupling bracket is configured to secure a handle to the removable portion of the fluid coupling assembly and to secure the removable portion of the fluid coupling assembly to the platform extension.

13. The probe assembly of claim 12, wherein the handle is positioned for gripping to assist with the simultaneous withdrawal of the interconnected probe platform, platform extension, removable portion of the fluid coupling assembly, handle, and coupling bracket from the probe assembly.

14. A probe assembly comprising a flange assembly, a probe platform, a platform extension, an extension enclosure, and a fluid coupling assembly, wherein:

the flange assembly is configured to mount the probe assembly to a stack fixture assembly of an exhaust stack;

the extension enclosure is configured to extend into a flow of particulate-containing gas passing through the exhaust stack when the probe assembly is mounted to the exhaust stack;

the probe platform is configured to support an analytical probe;

the platform extension at least partially supports the probe platform in the vicinity of a distal end of the extension enclosure;

the fluid coupling assembly comprises a removable portion and a retained portion;

the removable portion of the fluid coupling assembly comprises one or more disengageable fluid passages extending from an engaging interface of the removable portion to an input/output interface of the removable portion;

the retained portion of the fluid coupling assembly comprises one or more retained fluid passages extending from an input/output interface of the retained portion to an engaging interface of the retained portion;

the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly;

the probe platform, the platform extension, and the removable portion of the fluid coupling assembly are interconnected and are configured to be withdrawn simultaneously from the probe assembly independent of the retained portion of the fluid coupling assembly; and wherein the retained portion of the fluid coupling assembly comprises a securing interface configured to permit passage of securing hardware for the mounting of the retained portion to the probe assembly.

15. A probe assembly comprising a flange assembly, a probe platform, a platform extension, an extension enclosure, and a fluid coupling assembly, wherein:

the flange assembly is configured to mount the probe assembly to a stack fixture assembly of an exhaust stack;

the extension enclosure is configured to extend into a flow of particulate-containing gas passing through the exhaust stack when the probe assembly is mounted to the exhaust stack;

the probe platform is configured to support an analytical probe;

the platform extension at least partially supports the probe platform in the vicinity of a distal end of the extension enclosure;

the fluid coupling assembly comprises a removable portion and a retained portion;

the removable portion of the fluid coupling assembly comprises one or more disengageable fluid passages extending from an engaging interface of the removable portion to an input/output interface of the removable portion;

the retained portion of the fluid coupling assembly comprises one or more retained fluid passages extending from an input/output interface of the retained portion to an engaging interface of the retained portion;

the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly;

the probe platform, the platform extension, and the removable portion of the fluid coupling assembly are interconnected and are configured to be withdrawn simultaneously from the probe assembly independent of the retained portion of the fluid coupling assembly; and wherein the platform extension substantially traverses a length of the extension enclosure such that the platform extension extends from the vicinity of the distal end of the extension enclosure through an end of extension enclosure proximal to the flange assembly.

16. A probe assembly comprising a flange assembly, a probe platform, a platform extension, an extension enclosure, a fluid coupling assembly, a handle, and a coupling bracket, wherein:

the flange assembly is configured to mount the probe assembly to a stack fixture of an exhaust stack;

the extension enclosure is configured to extend into a flow of particulate-containing gas passing through the exhaust stack when the probe assembly is mounted to the exhaust stack;

the probe platform is configured to support an analytical probe;

the platform extension at least partially supports the probe platform in the vicinity of a distal end of the extension enclosure;

the fluid coupling assembly comprises a removable portion and a retained portion;

the removable portion of the fluid coupling assembly comprises one or more disengageable fluid passages extending from an engaging interface of the removable portion to an input/output interface of the removable portion;

the retained portion of the fluid coupling assembly comprises one or more retained fluid passages extending from an input/output interface of the retained portion to an engaging interface of the retained portion;

the engaging interface of the retained portion of the fluid coupling assembly cooperates with the engaging interface of the removable portion of the fluid coupling assembly such that, with engagement of the removable and retained portions, the respective fluid passages of the removable and retained portions form one or more integrated fluid channels configured to permit passage of fluid through the fluid coupling assembly;

the coupling bracket is configured to couple the handle to the removable portion of the fluid coupling assembly and to couple the removable portion of the fluid coupling assembly to the platform extension;

the probe platform, the platform extension, the removable portion of the fluid coupling assembly, the coupling bracket, and the handle are interconnected and are configured to be withdrawn simultaneously from the probe assembly independent of the retained portion of the fluid coupling assembly; and the handle is positioned for gripping to assist with the simultaneous withdrawal of the interconnected probe platform, platform extension, removable portion of the fluid coupling assembly, handle, and coupling bracket from the probe assembly.

17. The probe assembly of claim 16, wherein the removable portion of the fluid coupling assembly is configured such that the engaging interface of the removable portion and the input/output interface of the removable portion are oriented in non-parallel or substantially orthogonal planes.

18. The probe assembly of claim 16, wherein the probe assembly further comprises a control box configured to house the fluid coupling assembly, the handle, the coupling bracket, and a flow control system configured to control gas flow substantially throughout the probe assembly.

19. The probe assembly of claim 18, wherein the flange assembly comprises:
   a flange configured to secure the probe assembly to a flange of the stack fixture assembly of the exhaust stack,
   a plate configured to secure to the control box of the probe assembly, and
   a pipe configured to couple the flange and the plate and to permit passage therethrough of the extension enclosure of the probe assembly.

* * * * *